(12) United States Patent
Ashizawa et al.

(10) Patent No.: US 6,855,497 B2
(45) Date of Patent: Feb. 15, 2005

(54) DNA TEST FOR SCA-10

(75) Inventors: Tetsuo Ashizawa, Houston, TX (US); Tohru Matsuura, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 378 days.

(21) Appl. No.: 09/942,336

(22) Filed: Aug. 29, 2001

(65) Prior Publication Data

US 2002/0146713 A1 Oct. 10, 2002

Related U.S. Application Data

(60) Provisional application No. 60/229,406, filed on Aug. 31, 2000.

(51) Int. Cl.$^7$ .......................... C12Q 1/68; C12P 19/34; C12N 1/00; C07H 21/02; C07H 21/04

(52) U.S. Cl. ..................... 435/6; 435/91.2; 435/91.5; 435/810; 536/23.1; 536/24.3; 536/24.33

(58) Field of Search .................. 435/6, 91.2, 91.5, 435/91.51, 810; 536/23.1, 24.3, 24.33

(56) References Cited

U.S. PATENT DOCUMENTS

| | | | |
|---|---|---|---|
| 5,834,183 A | 11/1998 | Orr et al. | |
| 5,840,491 A | 11/1998 | Kakizuka | |
| 5,853,995 A | 12/1998 | Lee | |
| 5,981,185 A | 11/1999 | Matson et al. | |

OTHER PUBLICATIONS

Del–Favero, J. et al., "Isolation of CAG/CTG repeats from within the chromosome 2p21–p24 locus for autosomal dominant spastic paraplegia (SPG4) by YAC expansion", Hum. Genet., vol. 105, pp. 217–225 (Sep. 1999).*
Haaf, T. et al., "Chromosomal localization of long trinucleotide repeats in the human genome by fluorescence in situ hybridization", Nature Genet., vol. 12, pp. 183–185 (1996).*
Timchenko, LT and Caskey, CT; Trinucleotide repeat disorders in humans: discussions of mechanisms and medical issues; FASEB J., Dec. 1996, pp. 1589–1597; vol. 10(14).
Burgess, DL, Matasuura, T., Ashizawa, T., Noebels, JL; Genetic localization of the Ca2+ channel gene CACNG2 near SCA10 on chromosome 22q13; Epilepsia, Jan. 2000, pp. 24–27; vol, 14(1).
Silveira, I. Alonso, I., Guimaraes, L., et al. High germinal instability of the (CTG)n at the SCA8 locus of both expanded and normal alleles; Am. J. Hum. Genet., 2000, pp. 830–840; vol. 66.
Zu, L., Figueroa, K.P., Grewal, R., Pulst, S.–M. Mapping of a new autosomal dominant spinocerebellar ataxia to chromosome 22; Am. J. Hum. Genet. 1999, pp. 594–599, vol. 64.
Matsuura, T., Achari, M., Khajavi, M., Bachinski, L.L., Zoghbi, H., Ashizawa, T. Mapping of the gene for a novel spinocerebellar ataxia with pure cerebellar signs and epilepsy; Ann. Neurol., 1999, pp. 407–411.

Matsuura, T., Watase, K., Nagamitsu, S., Zoghbi, H.Y., and Ashizawa, T. Fine mapping of the spinocerebellar ataxia type 10 region and search for a polyglutamine expansion; Ann. Neurol. Sep. 1999; p. 480; vol. 46(3).
Pujana, M.A., Corral, J., Gratacos, M. et al., Spinocerebellar ataxias in Spanish patients: genetic analysis of familiar and sporadic cases; Hum. Genet. 1999, pp. 516–522; vol. 104.
Giunti, P., Stevanin, G., Worth, P.F., et al. Molecular and clinical study of 18 families with ADCA Type II: evidence for genetic heterogeneity and de novo mutation; Am. J. Hum. Genet. 1999, pp. 1594–1603, vol. 64.
Worth, P.F., Giunti, P., Gardner–Thorpe, C., et al. Autosomal dominant cerebellar ataxia Type III: linkage in a large British family to a 7.6–cM region on chromosome 15q14–21.3; Am. J. Hum. Genet., 1999, pp. 420–426, vol. 65.
Ishikawa, K., Mizusawa, H., Saito, M., Tanaka, H., et al. Autosomal dominant pure cerebellar ataxia. A clinical and genetic analysis of eight Japanese families. Brain 1996, pp. 1173–1182, vol. 119 (Pt. 4).
Klockgether, T., Wullner, U., Spauschus, A., and Evert, B; The molecular biology of the autosomal–dominant cerebellar ataxias; Mov. Disord. 2000, pp. 604–612, vol. 15(4).
David, G. et al. Cloning of the SCA7 gene reveals a highly unstable CAG repeat expansion; Nature Genet. 1997, pp. 65–70, vol. 17.
Holmes, S.E. et al. Expansion of a novel CAG trinucleotide repeat in the 5' region of PPP2R2B is associated with SCA12; Nature Genet. 1999, pp. 391–392, vol. 23.
Imbert, G. et al. Cloning of the gene for spinocerebellar ataxia 2 reveals a locus with high sensitivity to expanded CAG/glutamine repeats. Nature Genet. 1996, pp. 285–291, vol. 14.
Kawaguchi, Y. et al. CAG expansions in a novel gene for Machado–Joseph disease at chromosome 14q32.1. Nature Genet. 1994, pp. 221–228, vol. 8.
Orr H.T. et al., Expansion of an unstable trinucleotide CAG repeat in spinocerebellar ataxia type 1. Nature Genet. 1993, pp. 221–226, vol. 4.
Pulst S.M. et al., Moderate expansion of a normally biallelic trinucleotide repeat in spinocerebellar ataxia type 2. Nature Genet 1996, pp. 269–276, vol. 14.

(List continued on next page.)

*Primary Examiner*—Jeffrey Fredman
*Assistant Examiner*—Teresa Strzelecka
(74) *Attorney, Agent, or Firm*—Fulbright & Jaworski, LLP

(57) ABSTRACT

Included is a method for detecting spinocerebellar ataxia type 10 (SCA10) by measuring the presence or absence of a DNA expansion in a gene locus associated with spinocerebellar ataxia type 10. The method employs extracting DNA from a sample to be tested, amplifying the extracted DNA; and identifying the presence or absence of a DNA expansion in the amplified extension products. Also included in the present invention are a kit for diagnosis of SCA10 and non-human transgenic eukaryotes that are not expressing or overexpressing SCA10.

17 Claims, 9 Drawing Sheets

OTHER PUBLICATIONS

Nakamura K. et al. SCA17, a novel autosomal dominant cerebellar ataxia caused by an expanded polyglutamine in TATA–binding protein. Hum. Mol. Genet. 2001, pp. 1441–1448, vol. 10.

Sanpei K. et al. Identification of the spinocerebellar ataxia type 2 gene using a direct identification of repeat expansion and cloning technique, DIRECT. Nature Genet. 1996, pp. 277–284, vol. 14.

Zhuchenko O. et al. Autosomal dominant cerebellar ataxia (SCA6) associated with small polyglutamine expansions in the alpha 1A–voltage–dependent calcium channel. Nature Genet. 1997, pp. 62–69, vol. 15.

Matsuura T, Yamagata T, Burgess DL, Rasmussen A, Grewal RP, Watase K, Khajavi M, Zu L, Pulst SM, Alonso E, Noebels JL, Nelson DL, Zoghbi HY, Ashizawa T. Large expansion of ATTCT pentanucleotide repeat in spinocerebellar ataxia type 10. Ann Neurol 2000;48:416. Presented at the Plenary Session of the 125th American Neurological Association Annual Meeting, 2000, Abstract Submission faxed Jul. 15, 2003.

Matsuura T, Burgess DL, Yamagata T, Rasmussen A, Grewal RP, Watase K, Tsuji K, Khajavi M, MacCall A, Davis, CF, Yescas P, Zu L, Pulst SM, Alonso E, Noebels JL, Nelson DL, Zoghbi HY, Ashizawa T. Large expansion of ATTCT pentanucleotide repeat in spinocerebellar ataxia type 10 (SCA10). Am J Hum Genet 2000;67:55, Abstract submission faxed Jul. 15, 2003.

Koob, MD, Moseley ML, Schut, LJ, Benzow, KA, Bird, TD, Day, JW, Ranum, LPW. An untranslated CTG expansion causes a novel form of spinocerebellar ataxia (SCA8). Nat Genet. 1999, 21: 379–384.

Ashizawa T, Matsuura T, Rasmussen A, Grewal RP, Zu L, Pulst SM, Pandolfo M, Sasaki H, Volpini V, Yamagata T, Watase K, Burgess DL, Inoue K, Yescas P, Nagamitsu S, Momoi MY, Tashiro K, Zoghbi HY, Alonso E, Nelson DL. Founder effect of the Spinocerebellar ataxia type 10 mutation in the Mexican population. Am J. Hum Genet 2000;67:373, Abstract submission faxed Jul. 15, 2003.

* cited by examiner

US 6,855,497 B2

DNA TEST FOR SCA-10

This application claims priority to U.S. Provisional Patent Application No. 60/229,406, filed Aug. 31, 2000.

The U.S. Government has rights in the invention by virtue of grant number NS41547-01 from NIH/NINDS and Merit Review from VA.

FIELD OF THE INVENTION

The invention generally relates to the fields of genetics and molecular biology. In particular, the invention relates to the SCA10 gene and a method of diagnosis of spinocerebellar ataxia type 10.

BACKGROUND OF THE INVENTION

Autosomal dominant cerbellar ataxias (ADCAs) are currently classified into three groups based on the symptoms presented: ADCA I, ADCA II, and ADCA III. All ADCAs exhibit a degree of cerballar dysfunction. ADCA I is based on the presence of pyramidal and extra pyramidal symptoms, ophthalmoplegia or a combination thereof. ADCA II is based on the presence of retinopathy. ADCA III is based on the absence of the ADCA I and II symptoms (Zu et al., 1999). A number of SCA genes have been identified or mapped and designated by the HUGO nomenclature committee "spinocerebellar ataxia type n (SCAn)" where "n" refers to the numeric number in order of mapping; these genes include SCA1, SCA2, SCA4, SCA5, SCA6, SCA7, SCA8, SCA10, SCA11, SCA12, SCA13, SCA14, SCA15, SCA16 and SCA17. Additionally, two ADCA gene designated MJD (also known as SCA3) and DRPLA have been identified for Machado-Joseph disease and dentatorubral pallidolysian atrophy, respectively.(Silveira et al., 2000). Many of the SCA types are due to a mutation in one of the genes that involves a trinucleotide-rep eat expansion in the gene (Zu et al., 1999). The number of repeats often correlates with the age of onset and the severity of the symptoms (O'Sullivan Smith et al., 1999). Diseases other than ADCAs have also been shown to have an expanded trinucleotide repeat as the mutation. Suppression of transcription by a large intronic repeat expansion in Friedreich's ataxia where an expanded GAA repeat interferes with transcription of the FRDA gene has been documented (Bidichandani et al., 1998). Fragile X syndrome and FRAXE mental retardation are caused by CGG and CCG repeat expansion in the 5' untranslated region of the FMR1 and FMR2 gene, respectively. In DM1, an unstable CTG repeat expands up to several thousand copies in the 3' untranslated region of the DMPK gene (Wells et al., 1998). Spinocerebellar ataxia type 10 (SCA10) is characterized by gait and limb ataxia, dysarthria, nystagmus, and occasional seizures (Zu et al., 1999; O'Sullivan Smith et al., 1999). SCA10 shows anticipation, in which the onset of the disease is earlier with each passing generation. A pedigree of Mexican-American descent that exhibits spinocerebellar ataxia type 10 has been identified (Zu et al., 1999). SCA10 is believed to be the second most common autosomal dominant cerebellar ataxia after SCA2 in Mexico.

Spinocerebellar ataxia type 10 (SCA10) is an autosomal dominant disorder characterized by cerebellar ataxia and occasional seizures. Several other SCA subtypes show trinucleotide repeat expansions and prior to the present invention, it was not known whether SCA10 was due to a trinucleotide repeat expansion.

Genetic mapping studies in two families localized the SCA10 locus to chromosome 22q13-qter (Matsuura et al., 1999; Zu et al., 1999). Two recombination events narrowed the SCA10 region to a 2.7-cM region between D22S1140 and D22S1153 (Matsuura et al., 1999; Zu et al., 1999; Matsuura et al., 1999). Although the DNA sequence of the entire euchromatic part of human chromosome 22 has recently become available, there are still 11 gaps that remain to be sequenced (Dunham et al., 1999). D22S1160 and D22S1153 reside in one of these gaps. Nevertheless, two contigs composed of bacterial artificial chromosomes (BACs), phage P1-derived artificial chromosomes (PACs), and cosmids cover most of this region.

In two large families with SCA10, all patients exhibited pure cerebellar ataxia while 25% and 60% of patients in respective families had recurrent episodes of generalized motor seizures, complex partial seizures, or both (Matsuura et al., 1999; Zu et al., 1999). The clinical phenomenon, known as "anticipation," is common in dominantly inherited SCAs, in which expanded CAG repeats coding for polyglutamine tracts in respective genes are unstable and exhibit larger expansions in successive generations (Orr et al., 1993; Pulst, et al., 1996; Sanpei et al., 1996; Imbert et al., 1996; Kawaguchi et al., 1994; David et al., 1997). Expansion of CAG repeats are involved in SCAs 1, 2, 3, 6, 7, 12, or 17 (Orr et al., 1993; Pulst, et al., 1996; Sanpei et al., 1996; Imbert et al., 1996; Kawaguchi et al., 1994; David et al., 1997; Zhuchenko et al., 1997; Holmes et al., 1999; Nakamura et al., 2001) and expansion of the CTG repeat is found at the SCA8 locus (Koob et al., 1999).

Prior to the present invention, the type of and location of the repeat responsible for spinocerebellar ataxia type 10 were unknown. The present invention provides a diagnostic test for spinocerebellar ataxia type 10.

SUMMARY OF THE INVENTION

One aspect of the present invention a method of detecting spinocerebellar ataxia type 10 in a sample containing DNA from an individual to be tested comprising the step of measuring the presence or absence of DNA expansion at a gene locus associated with spinocerebellar ataxia type 10.

A further aspect of the present invention is the method of measuring the expansion comprising the steps of: extracting the DNA from a sample to be tested; amplifying the extracted DNA; and identifying the presence or absence of a DNA expansion in the amplified extension products. In an embodiment of the invention, the sample to be tested is selected from the group consisting of blood, semen, vaginal swabs, tissue, mixtures of body fluids, and any biological sample that contains DNA.

In an embodiment of the invention the amplification is by PCR and may use primers of the sequence of SEQ ID NO: 3 and SEQ ID NO: 4.

In another embodiment, the DNA expansion is measured by Southern blotting analysis of restriction enzyme digests of genomic DNA with a probe to the SCA10 locus. The restriction endonuclease may be selected from the group consisting of EcoRI, EcoRV, HindIII and BglI. The probe may be created by the use of primers of the sequence of SEQ ID NO: 6 and SEQ ID NO: 7.

In yet another embodiment, the DNA expansion is determined by pulsed field gel electrophoresis.

In yet another embodiment, the DNA expansion is determined by fluorescence in situ hybridization.

In an embodiment of the invention, the DNA expansion is comprised of a pentanucleotide repeat. The pentanucleotide repeat may be ATTCT. The number of the pentanucleotide repeat may be between 10 and 29 for unaffected individuals and greater than 800 for individuals affected with spinocerebellar ataxia type 10, with individuals having pentanucleotide repeats in between the normal and expanded range requiring additional study for a diagnosis of spinocerebellar ataxia type 10. Additional study includes examination for symptoms of spinocerebellar ataxia type 10.

A further aspect of the invention is a method of detecting pentanucleotide repeats in SCA10 comprising the steps of: isolating DNA from an individual to be tested; and performing PCR analysis using the primers of the sequence of SEQ ID NO: 3 and SEQ ID NO: 4. The pentanucleotide repeat may be ATTCT.

Another aspect of the invention is a method of diagnosing spinocerebellar ataxia type 10 comprising the steps of: isolating DNA from an individual to be tested; performing PCR analysis using the primers of the sequence of SEQ ID NO: 3 and SEQ ID NO: 4; assessing the number of ATTCT repeats based on comparison to DNA from an unaffected individual; and determining whether the number of ATTCT repeats is expanded in comparison to that of unaffected individuals.

Another aspect of the present invention is a method of diagnosing spinocerebellar ataxia type 10 comprising the steps of: isolating DNA from an individual to be tested; performing PCR analysis using the primers of the sequence of SEQ ID NO: 10 and SEQ ID NO: 11; and assessing whether the number of ATTCT repeats is expanded in comparison to that of unaffected individuals.

Another embodiment of the invention is a kit for diagnosis of spinocerebellar ataxia type 10 comprising primers suitable for amplifying SCA10 and an enzyme suitable for amplifying nucleic acids including various polymerases. The primers may be of the sequence of SEQ ID NO: 3 and SEQ ID NO: 4. In another embodiment, the primers may be of the sequence of SEQ ID NO: 10 and SEQ ID NO: 11.

Yet another embodiment is a kit for diagnosis of spinocerebellar ataxia type 10 comprising a probe capable of hybridizing to SCA10 and an enzyme suitable for amplifying nucleic acids including various polymerases to provide the probe to be used in a Southern blot. The probe may be created using primers of the sequence of SEQ ID NO: 6 and SEQ ID NO: 7.

Another object of the invention is to provide non-human transgenic eukaryotes for use in study of spinocerebellar ataxia 10.

An embodiment of the invention is a non-human transgenic eukaryote wherein the eukaryote is not expressing SCA10; or the ortholog thereof. The eukaryote may be a mammal, and more specifically, may be a mouse.

Another embodiment of the invention is a non-human transgenic eukaryote that is over-expressing SCA10; or the ortholog thereof as compared to a similar non-transgenic eukaryote. The eukaryote may be a mammal, and more specifically, may be a mouse.

Another embodiment of the invention is a non-human transgenic eukaryote that is expressing the ATTCT repeat array with or without the sequences flanking the array in the SCA10 gene, as compared to a similar non-transgenic eukaryote. The eukaryote may be a mammal, and more specifically, may be a mouse.

Other objects, features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF SUMMARY OF THE DRAWINGS

The following drawings form part of the present specification and are included to further demonstrate certain aspects of the present invention. The invention may be better understood by reference to one or more of these drawings in combination with the detailed description of specific embodiments presented herein.

SEQUENCE SUMMARY

Figure 1:
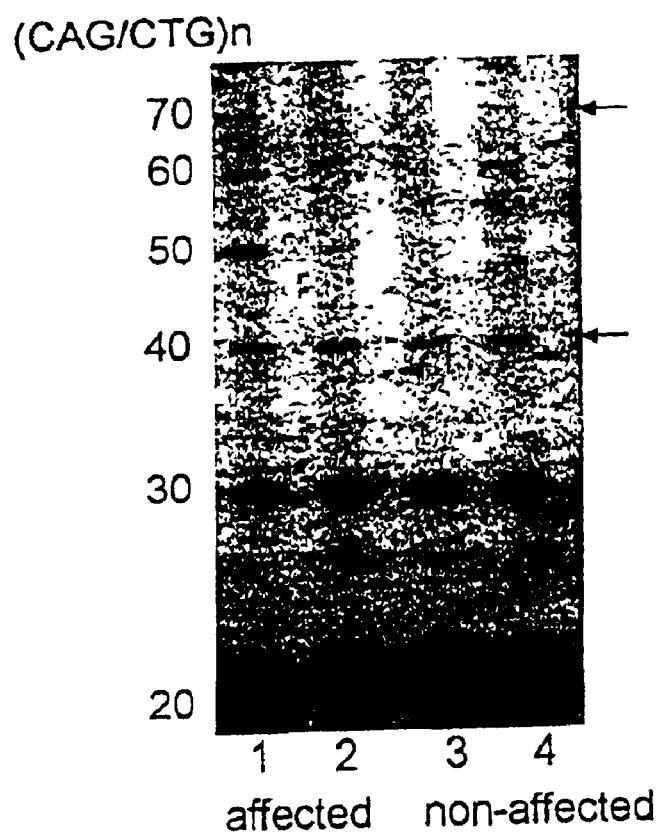
FIG. 1 shows repeat expansion detection (RED) analysis of affected and unaffected individuals.

SEQ ID NO: 1. Peptide sequence of human mouse Brain Protein E46-like sequence

SEQ ID NO: 2. Nucleotide sequence of the coding region of human mouse Brain Protein E46-like sequence SEQ ID NO: 3. Nucleotide sequence of attct-L primer SEQ ID NO: 4. Nucleotide sequence of attct-R primer SEQ ID NO: 5. Nucleotide sequence of ATTCT repeat SEQ ID NO: 6. Nucleotide sequence of DanL primer SEQ ID NO: 7. Nucleotide sequence of DanR primer SEQ ID NO: 8. Nucleotide sequence of E46A probe SEQ ID NO: 9. Nucleotide sequence of E46B probe SEQ ID NO: 10. Nucleotide sequence of forward primer for PCR SEQ ID NO: 11. Nucleotide sequence of reverse primer with hanging tail for PCR SEQ ID NO: 12. Nucleotide sequence of mE46A probe.

SEQ ID NO: 13. Nucleotide sequence for mE46B probe.

DETAILED DESCRIPTION OF THE INVENTION

The term "a" or "an" as used herein the specification may mean one or more. As used herein in the claim(s), when used in conjunction with the word "comprising", the words "a" or "an" may mean one or more than one. As used herein "another" may mean at least a second or more.

It will be readily apparent to one skilled in the art that various substitutions and modifications may be made to the invention disclosed herein without departing from the scope and the spirit of the invention.

As used in this application, the term "polynucleotide having the nucleic acid sequence of SEQ ID NO: 2" refers to a nucleic acid molecule that has been isolated free of total cellular nucleic acid. In some embodiments, the invention concerns a nucleic acid sequence essentially as set forth in SEQ ID NO: 2.

A functionally equivalent codon is a codon that encodes the same amino acid, such as the six codons for arginine or serine (Table 1), and also refers to codons that encode biologically equivalent amino acids.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The DNA segments of the present invention include those encoding biologically functional equivalent SCA10 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

Naturally, the present invention also encompasses DNA segments that are complementary, or essentially complementary, to the sequence set forth in SEQ ID NO: 2. Nucleic acid sequences that are "complementary" are those that are capable of base-pairing according to the standard Watson-Crick complementary rules. As used herein, the term "complementary" means nucleic acid sequences that are substantially complementary, as may be assessed by the same nucleotide comparison set forth above, or as defined as being capable of hybridizing to the nucleic acid segment of SEQ ID NO: 2 under relatively stringent conditions such as those described herein. Such sequences may encode the entire SCA10 protein or functional or non-functional fragments thereof.

"DNA expansion" as used herein, refers to an increase in the number of nucleotides found in a particular nucleotide sequence in comparison to that sequence in an individual that is not affected with the condition.

Hybridization

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1250, and 1500 bases and longer are contemplated as well. Such polynucleotides will find use, for example, as probes in Southern and Northern blots and as primers in amplification reactions.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Formamide and SDS also may be used to alter the hybridization conditions.

Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed.

Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In other embodiments, the probes or primers are labeled with radioactive species ($^{32}$P, $^{14}$C, $^{35}$S, $^{3}$H, or other label), with a fluorophore (rhodamine, fluorescein) or a chemiluminescent (luciferase).

One method of using probes and primers of the present invention is in the search for genes related to SCA10 or, more particularly, orthologs of SCA10 from other species. Normally, the target DNA will be a genomic or cDNA library, although screening may involve analysis of RNA molecules. By varying the stringency of hybridization, and the region of the probe, different degrees of homology may be discovered.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In other embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, it is envisioned that the probes or primers described herein will be useful as reagents in solution hybridization, as in PCR™, for detection of expression of corresponding genes, as well as in embodiments employing a solid phase. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety. Other methods of amplification are ligase chain reaction (LCR), Qbeta Replicase, isothermal amplification, strand displacement amplification (SDA), PCR-like template- and enzyme-dependent synthesis using primers with a capture or detector moiety, transcription-based amplification systems (TAS), cyclical synthesis of single-stranded and double-stranded DNA, "RACE", one-sided PCR, and di-oligonucleotide amplification.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of MRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Diagnosing Disorders Involving SCA10

SCA10 and the corresponding gene can be employed as a diagnostic or prognostic indicator of spinocerebellar ataxia type 10.

Genetic Diagnosis

One embodiment of the instant invention comprises a method for detecting variation in the number of pentanucleotide repeats in SCA10.

The methods described herein can be used to detect spinocerebellar ataxia type 10. The method comprises the steps of detecting variation of the (ATTCT), repeat found at the 3' end of intron 9 of the SCA10 gene by measuring the length of the repeat wherein n (number of repeats) for normal is in the range between 10 and 29 and n for spinocerebellar ataxia type 10 is in the range of greater than 800, with individuals having pentanucleotide repeats in between the normal and expanded range requiring additional study for a diagnosis of spinocerebellar ataxia type 10. Additional study includes examination for symptoms of spinocerebellar ataxia type 10.

The biological sample can be any tissue or fluid. Specifically, the biological sample includes blood, semen, vaginal swabs, buccal swabs, hair follicles, tissue, mixtures of body fluids and any biological sample that contains DNA. Yet other embodiments include dried blood spots, cells of the skin, muscle, fascia, brain, prostate, breast, endometrium, lung, thyroid, parathyroid, adrenal, head and neck, eye, pancreas, small intestine, blood cells, liver, testes, ovaries, colon, skin, stomach, esophagus, spleen, lymph node, bone marrow, thymus or kidney.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and/or polyA-selected RNA. Normally, the nucleic acid is amplified.

Depending on the format, the specific nucleic acids of interest are identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients. In this way, it is possible to correlate the amount of repeats detected with various clinical states.

Alterations of a gene include deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of SCA10 produced, both by altering the transcription of the gene or in destabilizing or otherwise altering the processing of either the transcript (mRNA) or protein.

A variety of different assays are contemplated in this regard, including but not limited to, PCR, fluorescent in situ hybridization (FISH), direct DNA sequencing, PFGE analysis, Southern blotting, and RFLP.

As used herein the term "polymerase chain reaction" or "PCR" refers to the PCR procedure described in the patents to Mullis, et al., U.S. Pat. Nos. 4,683,195 and 4,683,202. The procedure basically involves: (1)treating extracted DNA to form single-stranded complementary strands; (2)adding a pair of oligonucleotide primers, wherein one primer of the pair is substantially complementary to part of the sequence in the sense strand and the other primer of each pair is substantially complementary to a different part of the same sequence in the complementary antisense strand; (3)annealing the paired primers to the complementary sequence; (4)simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5)separating said extension products from said templates to produce single-stranded molecules; and (6)amplifying said single-stranded molecules by repeating at least once said annealing, extending and separating steps.

As used herein fluorescence in situ hybridization or "FISH" refers to the procedure described in Wott et al. (1988) and Kievits et al. (1990). The procedure basically involves the steps of preparing interphase or metaphase spreads from cells of peripheral blood lymphocytes and hybridizing labeled probes to the interphase or metaphase spreads. Using probes with mixed labels allows visualization of space, order and distance between hybridization sites. After hybridization the labels are examined to determine the order and distance between the hybridization sites.

As used herein, the term "pulsed field gel electrophoresis" or "PFGE" refers to a procedure described by Schwart et al. (1982). The procedure basically comprises running a standard electrophoresis gel (agarose, polyacrylamide or other gel known to those skilled in the art) under pulsing conditions. One skilled in the art recognizes that the strength of the field as well the direction of the field is pulsed and rotated in order to separate megabase DNA molecules. Current commercial systems are computer controlled and select the strength, direction and time of pulse depending on the molecular weight of DNA to be separated.

Measuring the amount or length of the repeat can be done by using FISH. In the FISH method, the repetitive sequence can be used as a probe to distinguish between normal and spinocerebellar ataxia type 10 syndrome simply by the presence or absence of a signal to the repetitive sequence. In this case, the application of the repeat sequence provides a sufficiently large target for the hybridization. Thus, it is possible that very sensitive FISH might detect affected individuals even though these would be lost to routine microscopy and detection. Although FISH is usually applied to metaphase nuclei, in the present invention it is applicable to both metaphase and interphase for the detection of spinocerebellar ataxia type 10.

Alternate methods to measure the repeat can include visual examination, densitometry measurement, quantitative radioactivity and quantitative fluorescence.

Southern/Northern Blotting

In one embodiment the size of the repeat is determined by Southern blotting analysis of restriction enzyme digests with probes contained within the SCA10 gene region.

One embodiment of the present invention is a method of detecting spinocerebellar ataxia type 10 syndrome comprising the steps of digesting DNA from an individual to be tested with a restriction endonuclease and detecting the restriction fragment length to polymorphism (RFLP) with hybridization to probes within the spinocerebellar ataxiatype 10.

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

Kit Components

All the essential materials and reagents required for detecting and sequencing SCA10 and variants thereof may be assembled together in a kit. This generally will comprise preselected primers and probes. Also included may be enzymes suitable for amplifying nucleic acids including various polymerases (RT, Taq, SequenaseTM etc.), deoxynucleotides and buffers to provide the necessary reaction mixture for amplification. Such kits also generally will comprise, in suitable means, distinct containers for each individual reagent and enzyme as well as for each primer or probe.

Transgenic Animals/Knockout Animals

In one embodiment of the invention, transgenic animals are produced which contain a functional transgene encoding a functional SCA10 polypeptide or variants thereof, or a transgene that is transcribed into an RNA but not translated into a protein. Transgenic animals expressing SCA10 transgenes can be used as models for studying spinocerebellar ataxia type 10.

In one embodiment of the invention, a SCA10 transgene is introduced into a non-human host to produce a transgenic animal expressing a human or murine SCA10 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual", 1994; which is incorporated herein by reference in its entirety).

It may be desirable to replace the endogenous SCA10 by homologous recombination between the transgene and the endogenous gene; or the endogenous gene may be eliminated by deletion as in the preparation of "knock-out" animals. Typically, a SCA10 gene flanked by genomic sequences is transferred by microinjection into a fertilized egg. The microinjected eggs are implanted into a host female, and the progeny are screened for the expression of the transgene. Transgenic animals are produced from the fertilized eggs from a number of animals including, but not limited to reptiles, amphibians, birds, mammals, and fish. Within a particular embodiment, transgenic mice are generated which overexpress SCA10 or express a mutant form of the polypeptide. Alternatively, the absence of a SCA10 in "knock-out" mice permits the study of the effects that loss of SCA10 protein has on a cell in vivo.

Promoter sequences may be used to drive expression of β-galactosidase or other reporter sequences such as green fluorescent protein, chloramphenicol acetyl transferase, and others known in the art. A reporter construct in transgenic mice is used to identify factors which regulate SCA10 expression.

One embodiment of the present invention is a method of detecting spinocerebellar ataxia type 10 comprising the step of measuring the presence or absence of DNA expansion at a gene locus associated with spinocerebellar ataxia type 10.

An embodiment of the present invention is the method of measuring the expansion comprising the steps of extracting the DNA from a sample to be tested, amplifying the extracted DNA, and identifying the presence or absence of a DNA expansion in the amplified extension products. The presence of a DNA expansion over the sequence found in unaffected individuals indicates the sample came from an individual with spinocerebellar ataxia. Suitable samples for testing include blood, semen, vaginal swabs, tissue, mixtures of body fluids, and any biological sample that contains DNA.

In an embodiment of the invention the amplification of the extracted DNA is by PCR and the primers are of the sequence of SEQ ID NO: 3 and SEQ ID NO: 4.

In another embodiment, the DNA expansion is measured by Southern blotting analysis of restriction enzyme digests with a probe to the SCA10 locus. The digest may be performed using the restriction endonucleases EcoRI, EcoRV, HindIII and BglI. The probe may be created by the use of primers of the sequence of SEQ ID NO: 6 and SEQ ID NO: 7.

In other embodiments, the DNA expansion is determined by pulsed field gel electrophoresis or fluorescence in situ hybridization.

The DNA expansion is comprised of a pentanucleotide repeat. The pentanucleotide repeat is of the sequence ATTCT and the length of the pentanucleotide repeat is between 10 and 29 for unaffected individuals and greater than 800 for individuals affected with spinocerebellar ataxia type 10, with individuals having pentanucleotide repeats in between the normal and expanded range requiring additional study for a diagnosis of spinocerebellar ataxia type 10. Additional study includes examination for symptoms of spinocerebellar ataxia type 10.

Another embodiment of the invention is a kit for diagnosis of spinocerebellar ataxia type 10 comprising primers suitable for amplifying SCA10 and an enzyme suitable for amplifying nucleic acids including various polymerases. The primers may be of the sequence of SEQ ID NO: 3 and SEQ ID NO: 4.

Another embodiment is a kit for diagnosis of spinocerebellar ataxia type 10 comprising a probe capable of hybridizing to SCA10 and an enzyme suitable for amplifying nucleic acids including various polymerases to provide the probe to be used in a Southern blot. The probe may be created using primers of the sequence of SEQ ID NO: 6 and SEQ ID NO: 7.

Another object of the invention is to provide non-human transgenic eukaryotes for use in study of spinocerebellar ataxia 10.

Another embodiments of the invention is a non-human transgenic eukaryote wherein the eukaryote is not expressing SCA10; or the ortholog thereof. Yet another embodiment is a non-human transgenic eukaryote that is over-expressing SCA10; or the ortholog thereof as compared to a similar non-transgenic eukaryote.

EXAMPLES

The following examples are included to demonstrate preferred embodiments of the invention. It should be appreciated by those of skilled the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. In the examples all percentages are by weight, if for solids and by volumes, if for liquids and all temperatures are in degrees Celsius unless otherwise noted.

Example 1

DNA Extraction And Polymorphism Analysis

DNA Was Extracted from Blood Samples of All Participants. Recombination events were defined and haplotypes were constructed by analyzing genomic DNA by PCR amplification of polymorphic simple sequence repeat (SSR) markers using end-labeled primers. The size of the PCR products were determined on 6% denaturing polyacrylamide gels.

Example 2

Repeat Expansion Detection (RED) Analysis

Because of the dominant inheritance of SCA10 and presence of anticipation, 14 trinucleotide repeats (>3 repeats in length) listed in the SCA10 candidate interval in the chromosome 22 genome database at the Sanger Centre (Dunham et al., 1999) were examined. None of these repeats showed expansions in the affected members of the families.

RED analysis (Schalling et al., 1993, Koob et al., 1998) was performed using genomic DNA samples of SCA10 patients and control subjects devoid of CAG/CTG expansions at the ERDA1 (chromosome 17) (Ikeuchi et al., 1998) and SEF2.1 (chromosome 18) (Breschel et al., 1997) loci. After 400 cycles of denaturing and annealing (95° C. for 10 s; 65° C. for 30 s) of 10 µg genomic DNA and $(CTG)_{10}$ or $(TTG)_{10}$ oligonucleotides in the presence of 5 U Ampligase (Epicentre), the product underwent electrophoresis and was then transferred to a nylon membrane. The membrane was hybridized with a $^{32}$P-end-labeled $(CAG)_{10}$ or $(CAA)_{10}$ oligonucleotide probe to detect tandemly ligated $(CTG)_{10}$ or $(TTG)_{10}$ oligonucleotides (FIG. 1). Repeat expansion detection (RED) analysis of genomic DNA samples from affected family members failed to show evidence of a CAG or CAA expansion. There was no difference between the affected (70, 40 repeats) and non-affected (40, 70 repeats).

Example 3

Western Blot Analysis

Protein extracts obtained from lymphoblastoid cell lines derived from SCA10 patients and control subjects were electrophoresed. After western blotting, the monoclonal antibody "1C2" raised against TATA-binding protein (Trottier et al., 1995) was used to look for expanded polyglutamine repeats.

Figure 2:
FIG. 2 shows a Western blot of SCA10 lymphoblastoid cells using mAb 1C2.

Proteins containing expanded polyglutamine tracts were not detected (FIG. 2). No detection of abnormal proteins in SCA10 lymphoblastoid cells (LCs) were found compared with the control. The mAb 1C2 raised against TATA-binding protein (TBP) detected ataxin-1 at 100 K in SCA1 LCs with a large CAG expansion (n=82) as well as TBP.

Example 4

PCR Assay of SCA10 Repeats

Figure 4:
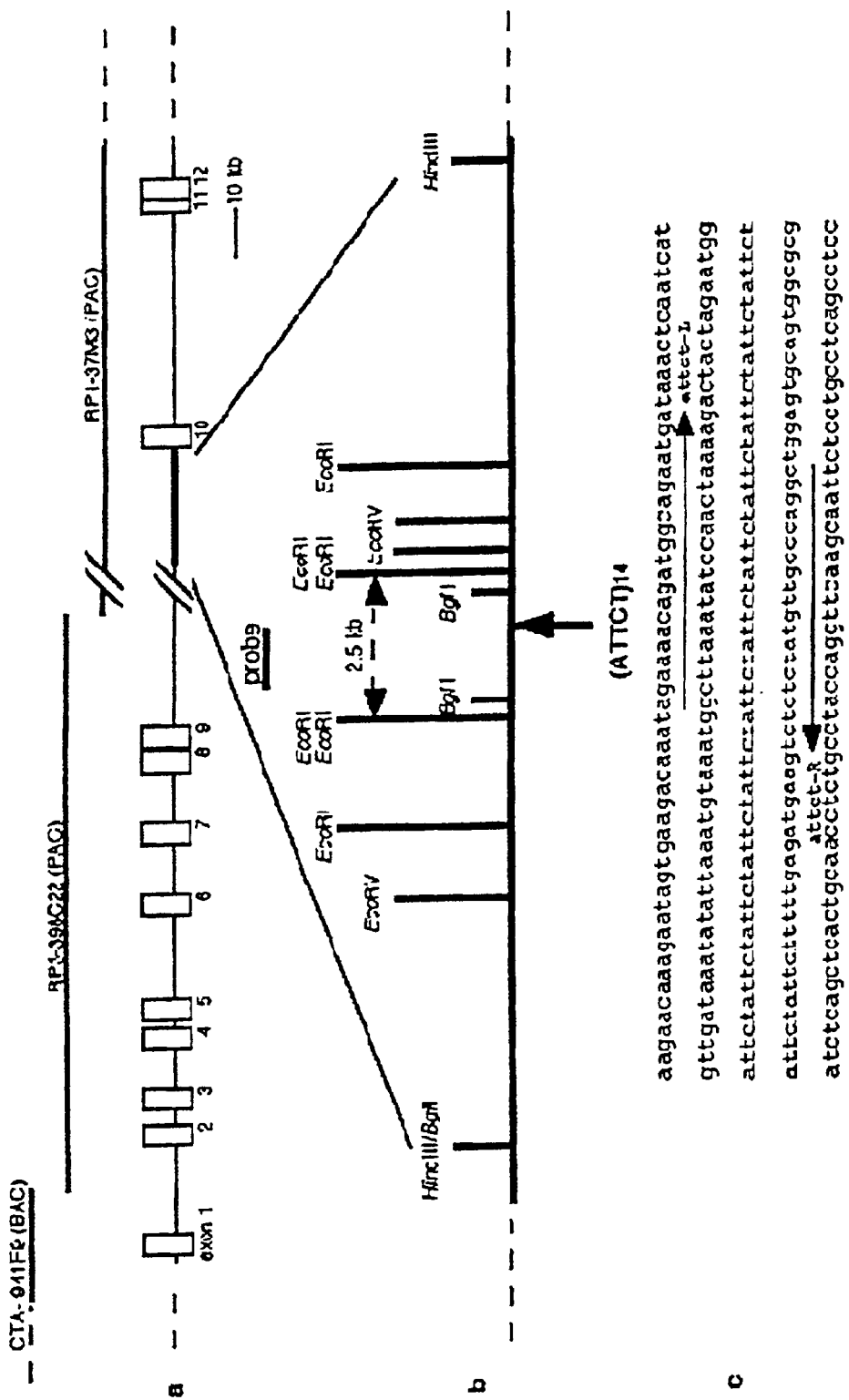
FIG. 4a shows a schematic presentation of the structure of the SCA10 gene.
FIG. 4b shows a restriction map of the ATTCT repeat region.
FIG. 4c shows the nucleotide sequence of ATTCT repeat.

The ATTCT repeat region from genomic DNA of affected and unaffected individuals was PCR-amplified using primers of the sequence (5'-AGAAAACAGATGGCAGAATGA-3') (SEQ ID NO:3) and (5'-GCCTGGGCAAC-ATAGAGAGA-3') (SEQ ID NO:4) in HotStarTaq Master Mix (Qiagen) including 10% DMSO (FIG. 4c). The PCR condition consisted of initial denaturing at 95° C. for 15 min, 30 PCR cycles (denaturing at 94° C. for 30 s, annealing at 54° C. for 30 s, extension at 72° C. for 45 s), and additional extension at 72° C. for 7 min. The PCR products from affected and unaffected individuals were sequenced using Applied Biosystems (ABI) automated sequencer with fluorescent dideoxynucleotides.

Figure 3:
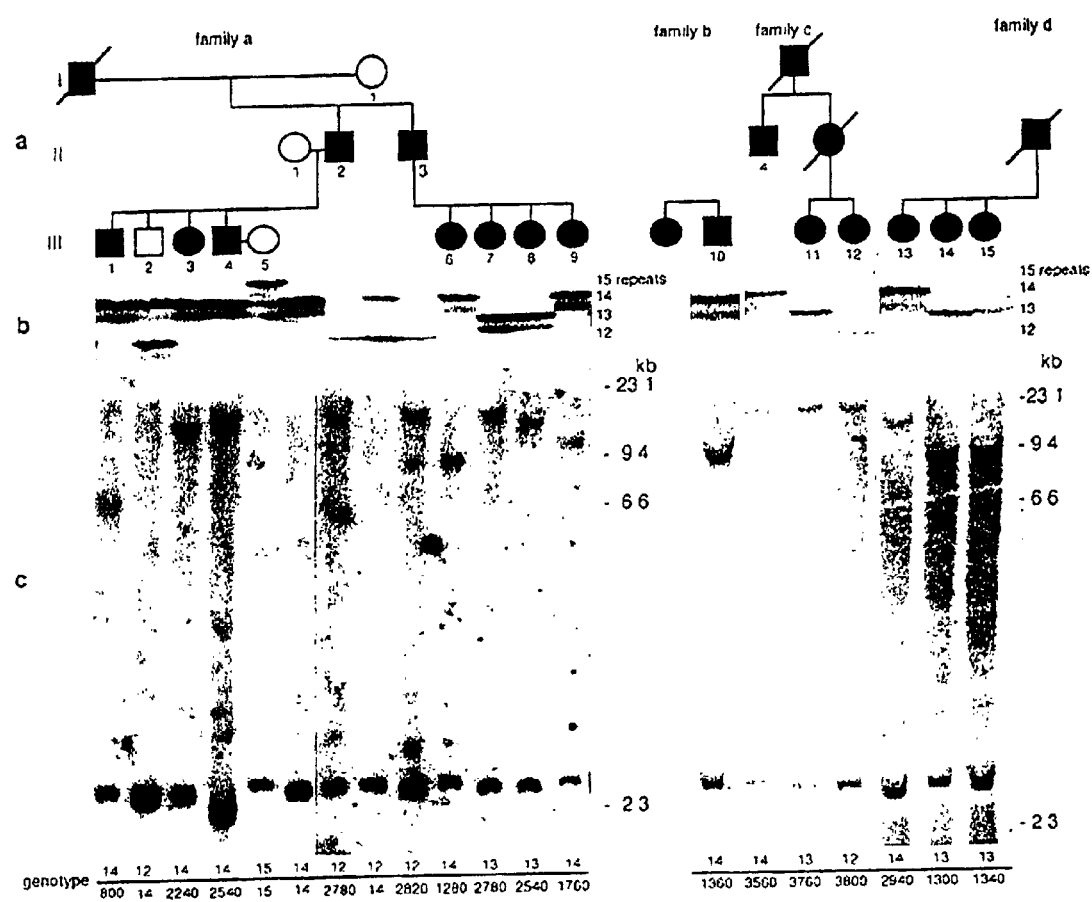
FIG. 3a shows pedigrees of four families studied for the SCA10 mutation.
FIG. 3b: shows PCR analysis of the ATTCT pentanucleotide repeat using primers of the sequence of SEQ ID NO:3 and SEQ ID NO:4.
FIG. 3c shows Southern analysis of expansion mutations of the ATTCT repeat region.

The ATTCT pentanucleotide repeat region was PCR-amplified from the genomic DNA samples of the family members indicated in FIG. 3a using primers of the sequence of SEQ ID NO: 3 (attct-L) and SEQ ID NO: 4 (attct-R). All affected individuals showed a single allele of variable size in families a, b, c and d (note that each band accompanies a shadow band underneath due to PCR artifact). In family a, two unaffected individuals (I-1 and III-2) are heterozygous and two spouses (II-1, III-5) are homozygous for the ATTCT repeat. In this family, affected individuals in the second generation (II-2 and II-3) failed to transmit their 12-repeat allele to their affected offspring (III-1, III-3, III-4, III-6, III-7, III-8 and III-9) while an unaffected offspring (III-2) received this allele from the affected father (II-2). The alleles of unaffected parents (I-1 and II-1) were passed on to their offspring in a pattern consistent with Mendelian inheritance. These data indicate that the affected individuals are apparently hemizygous for the ATTCT repeat.

Figure 5:
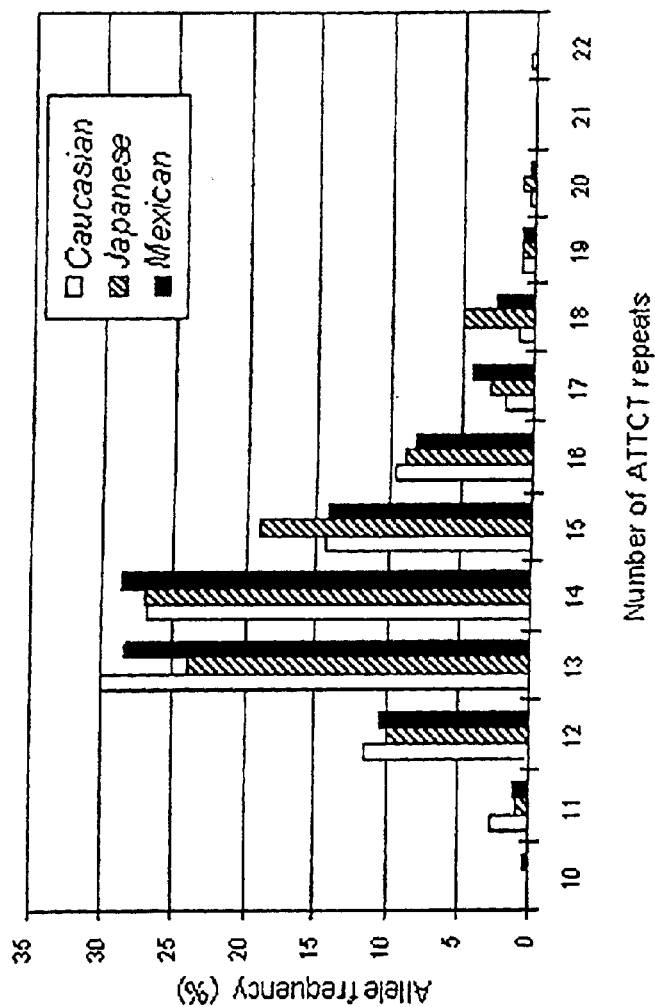
FIG. 5 shows distribution of the ATTCT repeat alleles in normal populations.

PCR analysis of the region spanning a pentanucleotide (ATTCT) tandem repeat in intron 9 of the SCA10 gene (previously designated E46) (FIG. 4) showed repeat number polymorphism in normal individuals (FIG. 3b, FIG. 5). Normal alleles contained from 10 to 20 repeats with 82.1% heterozygosity. Sequence analysis of the alleles obtained from 20 normal individuals showed tandem repeats of ATTCT without interruption. The distribution of the alleles was unimodal with similar patterns among the Caucasian, Mexican and Japanese populations examined (FIG. 5). The allele distributions in each of three ethnically defined populations (including 127 persons from the Mexican population) were consistent with the Hardy-Weinberg equilibrium (p>>0.05). In SCA10 families, PCR analysis demonstrated a uniform lack of heterozygosity in all affected individuals and carriers of the disease haplotype (Matsuura et al, 1999, Zu et al., 1999), with the single amplified allele of the ATTCT repeat being shared by their unaffected parent. When the affected and unaffected parents of the patients carried distinct ATTCT repeat alleles, the single allele amplified from the affected parent was never transmitted to any of these patients, indicating that the affected parent was hemizygous and that only the allele on the wild-type (non-SCA10) chromosome is amplified (FIG. 3b). Two other sets of primers flanking the ATTCT repeat gave the same result, excluding the possibility that the apparent hemizygosity is due to a mutation within the primer binding site.

Example 5

Southern Analysis

Southern blots of genomic DNA digested with multiple restriction enzymes, including EcoRI, EcoRV, HindIII and BglI, underwent hybridization to a non-repetitive probe obtained by PCR amplification of the region immediately upstream of the ATTCT repeat using DNA from a PAC clone (RP1-37M3) as template (FIG. 4b).

Ten µg of EcoRI-digested genomic DNA underwent 0.6% to 0.8% agarose gel electrophoresis followed by capillary transfer to the Hybond $N^+$ membrane (Amersham). An 800-bp SCA10 probe located upstream to the pentanucleotide repeat was generated by PCR using DNA of a PAC clone (RP1-37M3) as the template (FIG. 4b). Primers were: DanL (5'-TCCTTCCTCAGTCTTTCTGG-3') (SEQ ID NO: 6) and Danr (5'-TGCCATCTGTTTTCTATTTG-3') (SEQ ID NO: 7). Using the probe random prime labeled with $^{32}P$-α-dCTP (Amersham), the membrane was hybridized in Church buffer (0.1 mM EDTA at pH 8.0, 0.5 M sodium phosphate at pH 7.2, 7% SDS) at 60° C. overnight and analyzed by autoradiography after washing.

Southern blots of the genomic DNA samples digested with EcoRI using a 0.6% to 0.8% agarose gel show variably expanded alleles in affected members of the families shown above. All individual examined have a normal allele (2.5 kb). The apparent variability of the normal allele size is attributable to gel-loading artifacts since additional analyses using the same (EcoRI) and different (EcoRV, HindIII and BglI) restriction enzymes did not show consistent variability of the normal allele size. The genotype of each individual is shown at the bottom, with an estimated number of pentanucleotide repeats for disease-chromosomes based on the fragment size.

In addition to the expected normal allele, a variably expanded allele in all affected individuals was detected, while in all unaffected family members only the wild-type allele was detected, demonstrating that the ATTCT repeat region is expanded exclusively in SCA10 patients (FIG. 3c).

Example 6

Pentanucleotide Repeat Expansions

Three additional families with an autosomal dominant disease characterized by cerebellar ataxia and seizures were identified (FIG. 3a). The age of disease onset appeared to be earlier in successive generations in these families. This clinical phenomenon is known as "anticipation."

The inventors found an expansion of a pentanucleotide (ATTCT) repeat in intron 9 of the SCA10 gene, up to 19 kb larger than the normal allele, in all patients in five SCA10 families. Analysis of 562 chromosomes from unaffected individuals of various ethnic origins, showed a size range of 10 to 29 ATTCT repeats with no evidence of expansions. The data indicates that the novel SCA10 intronic ATTCT pentanucleotide repeat in SCA10 patients is unstable.

An SCA10 expansion mutation was not detected in 17 probands of unrelated Caucasian-American families with autosomal dominant cerebellar ataxia that have tested negative for the SCAs 1, 2, 3, 6, 7, 8 or 12 mutations.

Example 7

Physical Map of the ATTCT Pentanucleotide Repeat Region.

a: A Schematic Presentation of the Structure of the SCA10 Gene.

SCA10 consists of 12 exons which total 1971 base pairs. The ATTCT repeat is located in intron 9. The 12 exons of SCA10 span 172.8 kb of genomic DNA with an open reading frame (ORF) of 1428 bp, encoding 475 amino acids with no homology to known human proteins. Although human SCA10 is well-conserved with its presumed mouse ortholog (82% identity, 91% similarity over 475 amino acids), the next most similar sequence present in the GenBank database is a putative plant protein of unknown function identified by the Arabidopsis genome project (24% identical, 41% similar over 409 amino acids). Analysis of the SCA10 amino acid sequence indicates that this protein is a non-transmembrane globular protein without any nuclear localization signal or other type of signal peptide (Golgi, peroxisomal, vacuolar, or endoplasmic reticulum-retention). The gap at the left of PAC 37M3 does not represent missing sequence, but was introduced to preserve scale.

b: A Restriction Map of the ATTCT Repeat Region Defined by Flanking HindIII Restriction Sites (nt 17,023 and 34,567).

The numbers are nucleotide positions in the PAC37M3. "robe" indicates the position of the probe used (nt 25,222–26,021) to detect the 2.5 kb EcoRI fragment shown in FIG. 4b in the Southern analysis. The ATTCT repeat is located downstream of the probe within the 2.5 kb EcoRI fragment.

c: Nucleotide Sequence of the ATTCT Repeat (14 Repeats; Underlined, nt 26,101-26170) and the Flanking Regions (nt 25,981–26,281).

Arrows underline PCR primer sequences (attct-L, SEQ ID NO: 3) and (attct-R ,SEQ ID NO: 4) that were used for amplification of the ATTCT repeat region shown in FIG. 4c.

Example 8

Correlations

Figure 6:
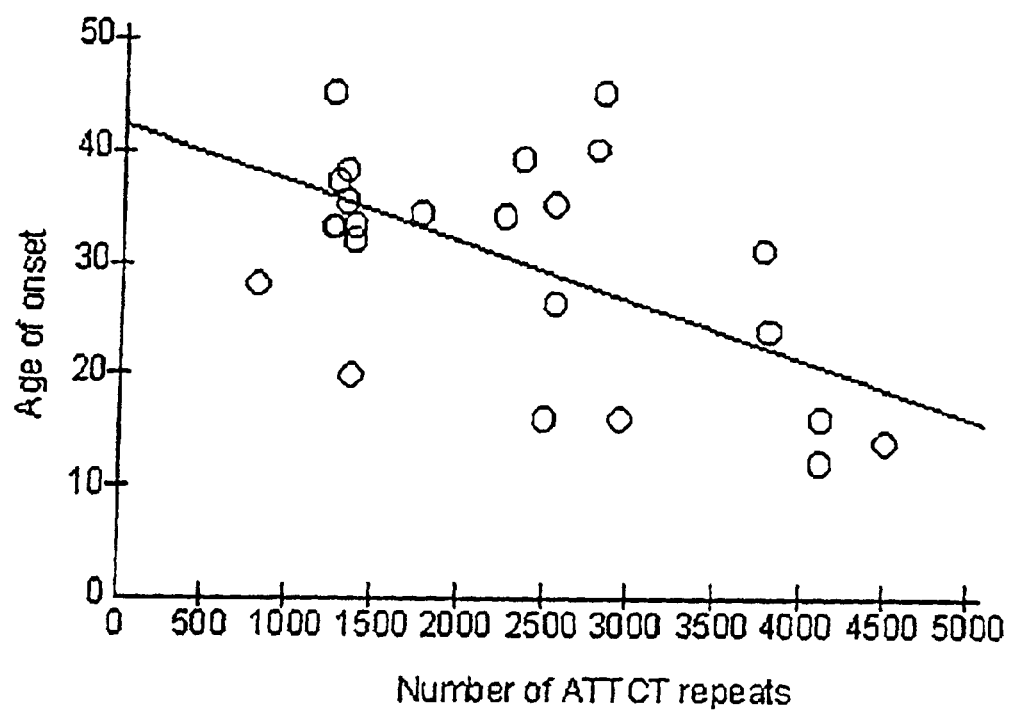
FIG. 6 shows correlation between the size of expanded SCA10 ATTCT repeat and the age of onset in 26 SCA10 patients.

The variable size of expanded alleles among affected individuals indicates the expanded ATTCT repeat is highly unstable. In the SCA10 families studied, intergenerational changes of the expanded alleles were variable, including not only expansions but also contractions (FIG. 3c). Haplotype analysis using DNA markers flanking the ATTCT repeat showed a single disease haplotype shared by all SCA10 families studied. A potentially important observation in the SCA10 families was the weak inverse correlation between the size of the expanded allele and the age of disease onset (n=26, $r^2$=0.34, p=0.018) (FIG. 6). The correlation argues against the possibility that the expansion represents a rare non-pathogenic polymorphism. Furthermore, there is no evidence of the ATTCT expansion in 562 normal chromosomes.

Example 9

Distribution of the ATTCT Repeat Qlleles in Normal Populations.

Shown is a histogram of the normal ATTCT repeat alleles in Caucasian (n=250), Japanese (n=100) and Mexican (n=254) chromosomes (FIG. 5). The distribution of the alleles was unimodal with similar patterns among the Caucasian, Mexican and Japanese populations examined.

There were, however, subtle differences between these populations. In the Mexican and Japanese populations, the 14-ATTCT-repeat allele was the modal allele with frequencies of 29% and 27%, respectively. In the Caucasian population, the 13-repeat allele was modal with a frequency of 30%.

Example 10

Correlation Between the Size of Expanded SCA10 ATTCT Repeat and the Age of Onset.

A scatter plot (FIG. 6) shows an inverse correlation between the size of expansion and the age of onset in 26 SCA10 patients ($r^2$=0.34, p=0.018). Each symbol represents an SCA10 patient, and the linear regression line is shown.

Example 11

In-situ Hybridization

Horizontal brain sections (12 μm) were fixed from male C57BL/6J mice in 4% paraformaldehyde in PBS followed by dehydration. Antisense oligonucleotide probes were end-labeled using terminal deoxynucleotidyl transferase (Promega) and [$\alpha$-$^{35}$S] dATP (1250 Ci/mmol; NEN) to a specific activity of ~$10^9$ dpm/μg. Hybridization solution contained 50% (v/v) Formamide, 4xSSC, 25 mM sodium phosphate, 1 mM sodium pyrophosphate, 10% dextran sulfate (w/v), 5xDenhardt's solution, 200 μg/ml sonicated herring sperm DNA (Promega), 100 μg/ml polyadenylic acid [5'] (Sigma-Aldrich) and 5x$10^2$ dpm of [$\alpha$-$^{35}$S] dATP-labeled probe. To monitor background hybridization, the inventors added 100-fold excess of unlabeled oligonucleotide to control sections. The sequence of the 45-mer probes was: mE46A 5'-CTGTTGTCTTCAGTGAGATTTCG-CACAGCATACACCACCCACTGC-3' (SEQ ID NO:12) and mE46B 5'-CACTGCAGAGATGAGAGGTCCGTG-AGATGGAATCTGAATGTGTTC-3' (SEQ ID NO:13). Sections were hybridized to probes overnight at 42° C., washed in 1xSSC (22° C., 20 min), 0.3xSSC (55° C., 40 min), and 2xSSC (22° C., 5 min) then dehydrated and expose to Kodak BioMax MR film for 1 week.

Figure 7:
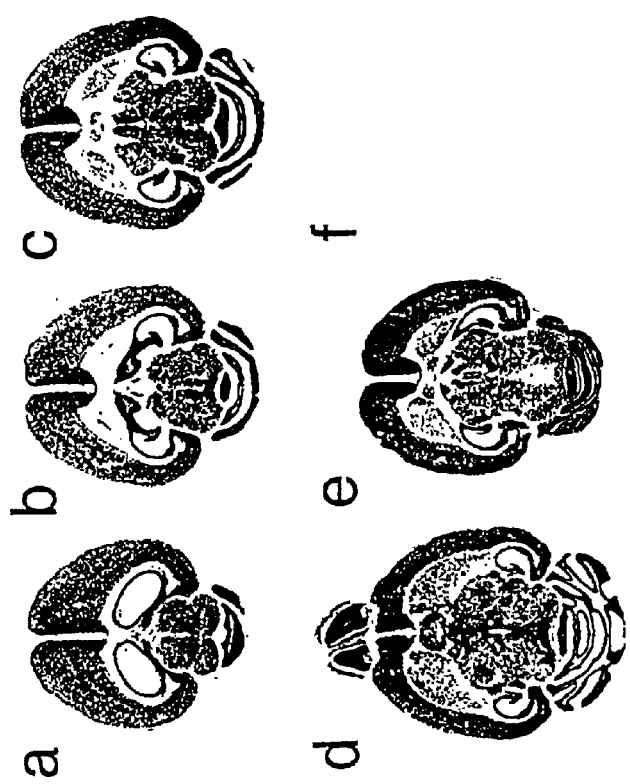
FIG. 7 shows in situ hybridization of radiolabeled probes to horizontal sections of 4-month-old adult (a–d) and 10 day old juvenile (e) mouse brain.

The in situ hybridization was to horizontal sections of 4-month-old adult (a–d) and 10 day old juvenile (e) mouse brain (FIG. 7). Expression was similar to the pattern of cell density determined by cresyl violet staining of the same sections. A–d: dorsal to ventral progression; f: negative control for non-specific hybridization to an adult brain section.

Example 12

SCA10 Expression

Figure 8:
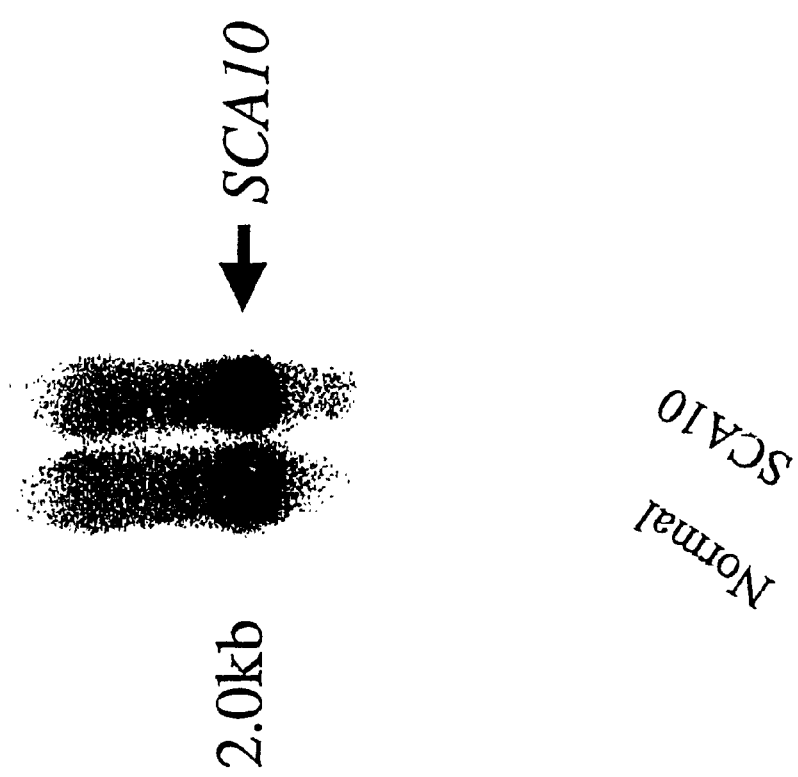
FIG. 8 shows a Northern blot of SCA10 MRNA in lymphoblastoid cell lines of SCA10 patients and unaffected individuals.

SCA10 is expressed widely in mammalian brain (FIG. 7), consistent with the phenotype of ataxia and epilepsy, and expressed sequence tags representing SCA10 are also detectable in several non-neuronal tissues. The northern blot data show no obvious changes in the level of SCA10 mRNA in lymphoblastoid cell lines of SCA10 patients (FIG. 8).

Example 13

PCR Amplification of Expanded ATTCT Repeat in SCA10

Unlike most ADCAs with triplet repeat (CAG/CTG) expansions, the mutation of SCA10 is an unstable expansion of an ATTCT pentanucleotide repeat (800 to about 4500 repeats; normal range 10–29 repeats). Because the expanded ATTCT repeat can give alleles of greater than 20 kb, which may be too large to be amplified by PCR, the molecular diagnosis of SCA10 can consist of two steps: 1) PCR analysis of the region spanning the ATTCT repeat to analyze the size of the normal alleles, and 2) Southern blot analysis to determine whether the ATTCT repeat is expanded in individuals showing a single allele by PCR. However, this method is laborious and costly and is difficult to use with degraded DNA samples or samples with a limited amount of DNA.

One aspect of the present invention is a simple PCR system that detects the expanded ATTCT allele with a characteristic ladder. The reaction was performed in 10 μl HotStarTaq Master Mix (Qiagen) containing 200 ng of genomic DNA as a template and 1 μM each of the primers. The $^{32}$P-end-labelled forward primer (GAAGACAA-ATAGAAAACAGATGGCAGA) (SEQ ID NO: 10) corresponds to a unique sequence upstream of the ATTCT repeat, while the reverse primer consists of a repeat sequence with a hanging tail sequence at its 5' end (TACGCATCCCAGTTTGAGACGG(AATAG)$_8$) (SEQ ID NO: 11) (Warner et al., 1996). The 5' hanging sequence has negligible complementarity to itself, AATAG or CTATT repeats, or any known human sequences. The repeat region at the 3' terminus of SEQ ID NO: 11 should randomly bind at multiple sites within the ATTCT repeat tract, generating a mixture of products that contain a variable number of repeats during the first PCR cycle. The hanging tail at the 5' end of the PCR products serve as an anchor that increases the probability for the reverse primer to anneal at the end of the repeat sequence during the subsequent cycles, preventing progressive shortening of the successive PCR products. The PCR conditions consisted of an initial denaturing at 95° C. for 15 min, 30 PCR cycles (94° C. for 30 s, 60° C. for 30 s, and 72° C. for 2 min), and additional extension at 72° C. for 10 min. PCR products were electrophoresed on 6% denaturing polyacrylamide gels and visualized by autoradiography.

Figure 9:
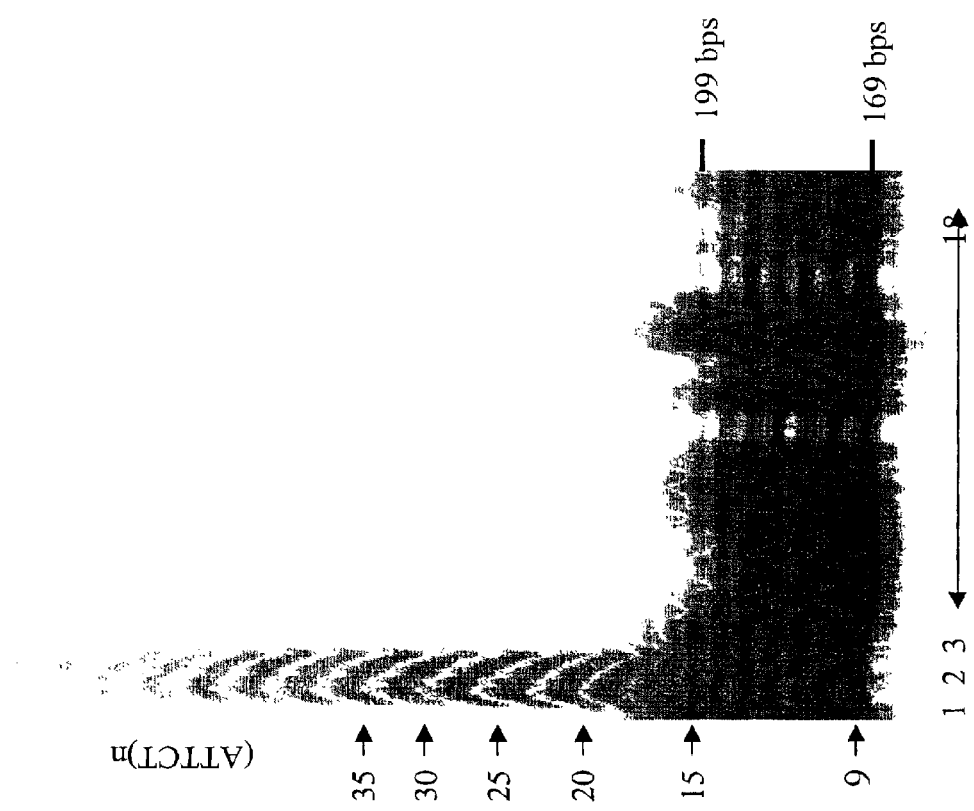
FIG. 9 shows PCR analysis of the ATTCT expansion in spinocerebellar ataxia type 10 (SCA10). Lanes 1 and 2 are for SCA10 patients, whereas lanes 3–18 are normal controls.

Analysis were performed on 44 SCA10 patients and 8 SCA10 mutation carriers confirmed by Southern blot and 100 normal controls whose ATTCT repeat alleles had been determined. Results of some of these analysis are shown in FIG. 9. All SCA10 patients showed continuous ladder exceeding the product range shown by normal controls. The repeat number of the largest product in the ladder corresponded to the known size of the larger allele in each normal control. There were no false positive results, i.e., no expansions in the normal controls. Moreover, expanded alleles were detected in highly degraded DNA samples of the three affecteds in two SCA10 pedigrees where Southern analysis failed to give a reliable result.

This analysis quickly and accurately identifies the mutation status of ATTCT repeat alleles. It easily distinguishes the individuals homozygous for normal alleles from SCA10 patients and reduces the number of samples that require the Southern blot analysis. This method is also useful for the cloning of the expanded alleles, which previously has been unsuccessful due to the massive size of the expansion. Uses of the cloned expanded repeats are for studies of the repeat structure and construction of the transgene containing the expanded ATTCT repeats. This PCR-based technology is useful for both genetic diagnosis and investigation of the disease mechanisms in SCA10.

SEQUENCE LISTING

<160> NUMBER OF SEQ ID NOS: 13

<210> SEQ ID NO 1
<211> LENGTH: 475
<212> TYPE: PRT
<213> ORGANISM: HUMAN

<400> SEQUENCE: 1

```
Met Ala Ala Pro Arg Pro Pro Ala Arg Leu Ser Gly Val Met Val
1               5                   10                  15

Pro Ala Pro Ile Gln Asp Leu Glu Ala Leu Arg Ala Leu Thr Ala Leu
                20                  25                  30

Phe Lys Glu Gln Arg Asn Arg Glu Thr Ala Pro Arg Thr Ile Phe Gln
            35                  40                  45

Arg Val Leu Asp Ile Leu Lys Lys Ser Ser His Ala Val Glu Leu Ala
        50                  55                  60

Cys Arg Asp Pro Ser Gln Val Glu Asn Leu Ala Ser Ser Leu Gln Leu
65                  70                  75                  80

Ile Thr Glu Cys Phe Arg Cys Leu Arg Asn Ala Cys Ile Glu Cys Ser
                85                  90                  95

Val Asn Gln Asn Ser Ile Arg Asn Leu Asp Thr Ile Gly Val Ala Val
                100                 105                 110

Asp Leu Ile Leu Leu Phe Arg Glu Leu Arg Val Glu Gln Glu Ser Leu
            115                 120                 125

Leu Thr Ala Phe Arg Cys Gly Leu Gln Phe Leu Gly Asn Ile Ala Ser
        130                 135                 140

Arg Asn Glu Asp Ser Gln Ser Ile Val Trp Val His Ala Phe Pro Glu
145                 150                 155                 160

Leu Phe Leu Ser Cys Leu Asn His Pro Asp Lys Lys Ile Val Ala Tyr
                165                 170                 175

Ser Ser Met Ile Leu Phe Thr Ser Leu Asn His Glu Arg Met Lys Glu
                180                 185                 190

Leu Glu Asn Leu Asn Ile Ala Ile Asp Val Ile Asp Ala Tyr Gln
            195                 200                 205

Lys His Pro Glu Ser Glu Trp Pro Phe Leu Ile Ile Thr Asp Leu Phe
        210                 215                 220

Leu Lys Ser Pro Glu Leu Val Gln Ala Met Phe Pro Lys Leu Asn Asn
225                 230                 235                 240

Gln Glu Arg Val Thr Leu Leu Asp Leu Met Ile Ala Lys Ile Thr Ser
                245                 250                 255

Asp Glu Pro Leu Thr Lys Asp Ile Pro Val Phe Leu Arg His Ala
                260                 265                 270

Glu Leu Ile Ala Ser Thr Phe Val Asp Gln Cys Lys Thr Val Leu Lys
        275                 280                 285

Leu Ala Ser Glu Glu Pro Pro Asp Asp Glu Ala Leu Ala Thr Ile
        290                 295                 300

Arg Leu Leu Asp Val Leu Cys Glu Met Thr Val Asn Thr Glu Leu Leu
305                 310                 315                 320

Gly Tyr Leu Gln Val Phe Pro Gly Leu Leu Glu Arg Val Ile Asp Leu
                325                 330                 335

Leu Arg Val Ile His Val Ala Gly Lys Glu Thr Thr Asn Ile Phe Ser
            340                 345                 350

Asn Cys Gly Cys Val Arg Ala Glu Gly Asp Ile Ser Asn Val Ala Asn
```

-continued

```
                355                 360                 365
        Gly Phe Lys Ser His Leu Ile Arg Leu Ile Gly Asn Leu Cys Tyr Lys
            370                 375                 380

Asn Lys Asp Asn Gln Asp Lys Val Asn Glu Leu Asp Gly Ile Pro Leu
        385                 390                 395                 400

Ile Leu Asp Asn Cys Asn Ile Ser Asp Ser Asn Pro Phe Leu Thr Gln
                        405                 410                 415

Trp Val Ile Tyr Ala Ile Arg Asn Leu Thr Glu Asp Asn Ser Gln Asn
                    420                 425                 430

Gln Asp Leu Ile Ala Lys Met Glu Glu Gln Gly Leu Ala Asp Ala Ser
                435                 440                 445

Leu Leu Lys Lys Val Gly Phe Glu Val Glu Lys Lys Gly Glu Lys Leu
        450                 455                 460

Ile Leu Lys Ser Thr Arg Asp Thr Pro Lys Pro
        465                 470                 475
```

<210> SEQ ID NO 2
<211> LENGTH: 1971
<212> TYPE: DNA
<213> ORGANISM: HUMAN

<400> SEQUENCE: 2

| | | |
|---|---|---|
| ggctcagcct agagctctcc ggcggcggcg cagcttcagg gcagcgcggg ctgcagcggc | 60 |
| ggcggcggtt agggctgtgt agggcgaggc ctccccttc ctcctcgcca tcctactcct | 120 |
| ccctcctcgt catcctcccc cttcgtcctc ctcgccttcc tcctcctcgt caggctcgac | 180 |
| ccagctgtga gcggcaagat ggcggcgccc aggccgccgc ctgccaggct gtcgggcgtc | 240 |
| atggtgccgg cgcccatcca agacctggag gccctgcgcg cgctcacggc gctcttcaaa | 300 |
| gagcagcgga accgagaaac agcacccagg actatcttcc aaagagttct ggatatccta | 360 |
| aagaaatctt ctcatgctgt tgagcttgcc tgccagagat ccatcccaag tggaaaacct | 420 |
| gcttccagtc tgcagttaat aacagaatgc ttcaggtgtc ttcgcaatgc ttgcatagag | 480 |
| tgttctgtga accagaattc aatcaggaac ttggatacga ttggtgttgc tgttgatttg | 540 |
| attcttctgt tcgtgaact gcgagtggaa caggaatctc tgttgacagc ttttcgctgt | 600 |
| ggcctgcagt ttttaggcaa cattgcctca cggaatgaag attcccagtc tattgtttgg | 660 |
| gtgcatgctt cccagaact gttttttgtct tgcttaaatc atccggacaa aaaaattgtt | 720 |
| gcctactctt caatgatttt gtttacatcc cttaatcatg aaagaatgaa agaactggag | 780 |
| gagaacctca atattgcaat tgatgtcata gatgcttacc aaaaacatcc tgaatcagaa | 840 |
| tggccgttct tgattattac agacctcttt ctgaaaagcc cggaattggt acaagccatg | 900 |
| tttcccaaac tgaacaatca gaaagagtt acactgttag accttatgat agccaagata | 960 |
| acgagtgatg agccactcac caaggatgac atccctgtgt ttttgcggca tgctgagttg | 1020 |
| attgcaagca ccttgtgga tcagtgcaag actgtgctca agctggcctc tgaggagcct | 1080 |
| cctgatgatg aggaggcact ggctacaatt aggcttctcg acgtcctgtg cgaaatgact | 1140 |
| gtgaatactg agctgctcgg ctatctgcag gttttccctg gcttgctgga agagtgatt | 1200 |
| gatcttttgc gggtgattca tgtagctgga aagaaaccaa caaacatctt cagtaattgt | 1260 |
| ggttgcgtga gagcagaagg tgacatctcc aatgtggcca atgggtttaa gtctcatctc | 1320 |
| attcgtctga ttggaaatct gtgttacaag aataaagata accaagacaa ggtaaatgag | 1380 |
| ctggatggta tcccgttgat cctggacaac tgcaacatca gtgacagtaa cccctttctg | 1440 |

-continued

```
acccagtggg tgatatatgc catccgaaac cttaccgaag acaacagcca aaaccaagat    1500
ttgattgcaa agatggagga acaggggctg gcagatgcat ccctacttaa aaaagtgggt    1560
tttgaagttg aaaagaaagg cgaaaagctg atcctgaaat ctactagaga cacccctaag    1620
ccatgaatga actacatcca aatacctgaa tttttggaat ctgtttcatg gattttcat     1680 cttctaccgt atgtgaaatt gcaagtgttt gaagatttat aagtacaaat ttgggaacat    1740
acaaatcttt taggtagtag agtttaacgt gtataagcta aaagtgaaag taactgagtg    1800
ttctcttgtt tctttgcatt aatgtaactg tgtggtttgc ctttgtcccc ctggatagaa    1860
cgtgcattta agaatatat tgtacttact gtgacagcag ataataaacc agtctcttgg     1920
agggcaaaaa aaaaaaaaa aaaaaaaaa aaaaaaaaa aaaaaaaaa a                 1971
```

<210> SEQ ID NO 3
<211> LENGTH: 21
<212> TYPE: DNA
<213> ORGANISM: PRIMERS

<400> SEQUENCE: 3

```
agaaaacaga tggcagaatg a                                              21
```

<210> SEQ ID NO 4
<211> LENGTH: 20
<212> TYPE: DNA
<213> ORGANISM: PRIMERS

<400> SEQUENCE: 4

```
gcctgggcaa catagagaga                                                20
```

<210> SEQ ID NO 5
<211> LENGTH: 197
<212> TYPE: DNA
<213> ORGANISM: HUMAN

<400> SEQUENCE: 5

```
agaaaacaga tggcagaatg ataaactcaa tcatgttgat aaatatatta aatgtaaatg    60
gcttaaatat ccaactaaaa gactactaga atggattcta ttctattcta ttctattcra   120
ttcrattcta ttctattcta ttctattcta ttctattcta ttcttttttga gatgaagtct   180 ctctatgttg cccaggc                                                   197
```

<210> SEQ ID NO 6
<211> LENGTH: 20
<212> TYPE: DNA
<213> ORGANISM: PRIMERS

<400> SEQUENCE: 6

```
tccttcctca gtctttctgg                                                20
```

<210> SEQ ID NO 7
<211> LENGTH: 20
<212> TYPE: DNA
<213> ORGANISM: PRIMERS

<400> SEQUENCE: 7

```
tgccatctgt tttctatttg                                                20
```

<210> SEQ ID NO 8
<211> LENGTH: 45
<212> TYPE: DNA
<213> ORGANISM: PROBES

```
<400> SEQUENCE: 8
ctgttgtctt cagtgagatt tcgcacagca tacaccaccc actgc                    45

<210> SEQ ID NO 9
<211> LENGTH: 45
<212> TYPE: DNA
<213> ORGANISM: PROBES

<400> SEQUENCE: 9
cactgcagag atgagaggtc cgtgagatgg aatctgaatg tgttc                    45

<210> SEQ ID NO 10
<211> LENGTH: 27
<212> TYPE: DNA
<213> ORGANISM: PRIMERS

<400> SEQUENCE: 10
gaagacaaat agaaaacaga tggcaga                                        27

<210> SEQ ID NO 11
<211> LENGTH: 52
<212> TYPE: DNA
<213> ORGANISM: PRIMERS

<400> SEQUENCE: 11
tacgcatccc agtttgagac ggaatagaat agaatagaat agaatagaat ag            52

<210> SEQ ID NO 12
<211> LENGTH: 45
<212> TYPE: DNA
<213> ORGANISM: MOUSE

<400> SEQUENCE: 12
ctgttgtctt cagtgagatt tcgcacagca tacaccaccc actgc                    45

<210> SEQ ID NO 13
<211> LENGTH: 45
<212> TYPE: DNA
<213> ORGANISM: MOUSE

<400> SEQUENCE: 13
cactgcagag atgagaggtc cgtgagatgg aatctgaatg tgttc                    45
```

REFERENCES

The following references, to the extent that they provide exemplary procedural or other details supplementary to those set forth herein, are specifically incorporated herein by reference:

U.S. Pat. No. 4,683,195
U.S. Pat. No. 4,683,202
U.S. Pat. No. 4,800,159
U.S. Pat. No. 5,843,663
U.S. Pat. No. 5,900,481
U.S. Pat. No. 5,919,626
U.S. Pat. No. 5,849,481
U.S. Pat. No. 5,849,486
U.S. Pat. No. 5,851,772
U.S. Pat. No. 4,873,191
WO 90/07641

Afrymax Technology

Bellus et al., 1994

Bidichandani S. I., Ashizawa T. & Patel, P. I. The GAA triplet-repeat expansion in Friedreich ataxia interferes with transcription and may be associated with an unusual DNA structure. Am. J. Hum. Genet. 62, 111–121 (1998).

Breschel T. S. et al. A novel, heritable, expanding CTG repeat in an intron of the SEF2-1 gene on chromosome 18q21.1. Hum. Mol. Genet. 6, 1855–1863 (1997).

David G. et al. Cloning of the SCA7 gene reveals a highly unstable CAG repeat expansion. Nature Genet. 17, 65–70 (1997).

Dunham I. et al. The DNA sequence of human chromosome 22. Nature 402, 489–495 (1999).

Freifelder D, and Better M. (1982) Dialysis of small samples in agarose gels. Anal Biochem. 123(1):83–5.

Higuchi R, Fockler C, Dollinger G, Watson R. (1993) Kinetic PCR analysis: real-time monitoring of DNA amplification reactions. Biotechnology (N.Y.). Sep; 11(9):1026–30.

Hogan, Beddington, Costantimi and Long, eds, Manipulating the Mouse Embryo; A Laboratory Manual" 2nd edition Cold Spring Harbor Laboratory Press, 1994.

Holmes S. E. et al. Expansion of a novel CAG trimicleotide repeat in the 5' region of PPP2R2B is associated with SCA12. Nature Genet. 23, 391–392 (1999).

Ikeuchi T., et al. A novel long and unstable CAG/CTG trinucleotide repeat on chromosome 17q. Genomics. 49, 321–326 (1998).

Imbert G. et al. Cloning of the gene for spinocerebellar ataxia 2 reveals a locus with high sensitivity to expanded CAG/glutamine repeats. Nature Genet 14, 285–291 (1996).

Innis et al., PCR Protocols, Academic Press, Inc., San Diego Calif., 1990.

Kawaguchi Y. et al. CAG expansions in a novel gene for Machado-Joseph disease at chromosome 14q32.1, Nature Genet 8, 221–228 (1994).

Kievits, et al., Cytogenet. Cell Genet, 53134–136 (1990).

Koob M. D. et al. An untranslated CTG expansion causes a novel form of spinocerebellar ataxia (SCA8). Nature Genet. 21, 379–384 (1999).

Koob M. D. et al. Rapid cloning of expanded trinucleotide repeat sequences from genomic DNA. Nature Genet. 18, 72–75 (1998).

Matsuura T, Yamagata T, Burgess D L, et al. Large expansion of ATTCT pentanucleotide repeat in spinocerebellar ataxia type 10. Nature Genet 2000; 26:191–194.

Matsuura T. et al. Mapping of the gene for a novel spinocerebellar ataxia with pure cerebellar signs and epilepsy. Ann. Neurol. 45, 407–411 (1999).

Matsuura T., Watase K., Nagamitsu S., Zoghbi H. Y. & Ashizawa T. Fine mapping of the spinocerebellar ataxia type 10 region and search for a polyglutamine expansion. Ann. Neurol. 46, 480 (1999).

Nakamura K., et al. SCA17, a novel autosomal dominant cerebellar ataxia caused by an expanded polyglutamine in TATA-binding protein. Hum. Mol Genet. 10:1441–1448 (2001).

O'Sullivan Smith et al., Spinocerebellar Ataxia: Making an Informed Choice About Genetic Testing, National Institute on Disability and Rehabilitation Research, Washington, D.C.(1999).

Orr H. T. et al. Expansion of an unstable trinucleotide CAG repeat in Spinocerebellar ataxia type 1, Nature Genet. 4, 221–226 (1993).

Palmiter R D, Brinster R L (1985) Transgenic mica Cell. 41 (2):343–5.

Pulst S. M. et al. Moderate expansion of a normally biallelic trinucleotide repeat in Spinocerebellar ataxia type 2. Nature Genet. 14, 269–276 (1996).

Sambrook et al., Molecular Cloning, 2nd ed., Cold Spring Harbor Laboratory Press, CSH, 1.38–1.39, 1989.

Sanpei K. et al. Identification of the Spinocerebellar ataxia type 2 gene using a direct identification of repeat expansion and cloning technique, DIRECT. Nature Genet 14, 277–284 (1996).

Schalling M., Hudson T. J., Buetow K. H. & Housman D. E. Direct detection of novel expanded trinucleotide repeats in the human genome. Nature Genet 4, 135–139 (1993), Schwartz, et al., Cold Springs Harbor Symposium, Quantitative Biology, 47:189–195 (1982).

Trottier Y. et al. Polyglutamine expansion as a pathological epitope in Huntington's disease and four dominant cerebellar ataxias. Nature 378, 403–406 (1995).

Warner J P, Barron L H, Goudie D, et al. A general method for the detection of large CAG repeat expansions by fluorescent PCR. J Med Genet 1996; 33:1022–1026. Wells R. D. & Warren S. T. Genetic instability and hereditary neurological diseases. San Diego, Academic Press (1998).

Wotta, et al., Am. J. of Human Genetics, 46, 95–106 (1988).

Zhuchenko O. et al. Autosomal dominant cerebellar ataxia (SCA6) associated with small polyglutamine expansions in the alpha 1A-voltage-dependent calcium channel. Nature Genet. 15, 62–69 (1997).

Zu L., Figueroa K. P., Grewal R. & Pulst S. M. Mapping of a new autosomal dominant spinocerebellar ataxia to chromosome 22. Am. J. Hum. Genet. 64, 594–599 (1999).

Zuhlke C, et al. Different types of repeat expansion in the TATA-binding protein gene are associated with a new form of inherited ataxia, Our. J. Hum. Genet. 9:160–164 (2001).

We claim:

1. A method of detecting spinocerebellar ataxia type 10 in a sample containing DNA from an individual to be tested comprising the step of measuring the presence or absence of DNA expansion at a spinocerebellar ataxia type 10 gene locus.

2. The method of claim 1, wherein the expansion is measured by the steps of:
   extracting the DNA from a sample to be tested;
   amplifying the extracted DNA; and
   identifying the presence or absence of a DNA expansion in the amplified extension products.

3. The method of claim 1, wherein the sample to be tested is selected from the group consisting of blood, semen, saliva, sweat, urine, nipple aspirates, vaginal swabs, tissue, or a combination thereof.

4. The method of claim 1, wherein the amplifying steps is by PCR.

5. The method of claim 4, wherein primers for the PCR are of the sequence of SEQ ID NO: 3 and SEQ ID NO: 4.

6. The method of claim 1, wherein the DNA expansion is measured by Southern blotting analysis of restriction enzyme digests with a probe to the SCA10 locus.

7. The method of claim 6, wherein the restriction enzyme is selected from the group consisting of EcoRI, EcoRV, HindIII and BglI.

8. The method of claim 6, wherein the probe is created by the use of primers of the sequence from the group consisting of SEQ ID NO: 6 and SEQ ID NO: 7.

9. The method of claim 1, where the DNA expansion is determined by pulsed field gel electrophoresis.

10. The method of claim 1, where the DNA expansion is determined by fluorescence in situ hybridization.

11. The method of claim 1, where the DNA expansion is comprised of a pentanucleotide repeat.

12. The method of claim 1, where the pentanucleotide repeat is ATTCT.

13. The method of claim 12, wherein the pentanucleotide repeat is repeated between 10 and 29 times for unaffected individuals and greater than 800 times for individuals affected with spinocerebellar ataxia type 10, with individuals having pentanucleotide repeats in between the normal and expanded range requiring additional study for a diagnosis of spinocerebellar ataxia type 10.

14. A method of detecting pentanucleotide repeats in SCA10 comprising the steps of:
   isolating DNA from an individual to be tested; and
   performing PCR analysis using the primers of the sequence from the group consisting of SEQ ID NO: 3 and SEQ ID NO: 4, wherein said PCR analysis detects said pentanucleotide repeats.

15. The method of claim 14 wherein the pentanucleotide repeat is ATTCT.

16. A method of diagnosing spinocerebellar ataxia type 10 comprising the steps of:

isolating DNA from an individual to be tested;

performing PCR analysis using the primers of the sequence from the group consisting of SEQ ID NO: 3 and SEQ ID NO: 4;

assessing the number of ATTCT repeats based on comparison to DNA from an unaffected individual; and determining whether the number of ATTCT repeats is expanded in comparison to that of unaffected individuals, wherein when said ATTCT repeats are expanded, said spinocerebellar ataxia type 10 is diagnosed.

17. A method of diagnosing spinocerebellar ataxia type 10 comprising the steps of:

isolating DNA from an individual to be tested;

performing PCR analysis using the primers of the sequence from the group consisting of SEQ ID NO: 10 and SEQ ID NO: 11; and assessing whether the number of ATTCT repeats is expanded in comparison to that of unaffected individuals, wherein when said ATTCT repeats are expanded said spinocerebellar ataxia type 10 is diagnosed.

* * * * *